United States Patent [19]
Barer et al.

[11] 4,055,663
[45] Oct. 25, 1977

[54] HALOGENATED ACYLAMINO ACIDS AS FUNGICIDES

[75] Inventors: Sol J. Barer, Plainsboro; Peter C. Valenti, East Windsor; Michael Marchwinski, N. Brunswick, all of N.J.

[73] Assignee: National Patent Development Corporation, New York, N.Y.

[21] Appl. No.: 483,579

[22] Filed: June 27, 1974

[51] Int. Cl.² .............................................. A01N 9/20
[52] U.S. Cl. .................................................. 424/319
[58] Field of Search ......................................... 424/319

[56] References Cited
U.S. PATENT DOCUMENTS 2,901,399  8/1959  Clarey .................................. 424/319

OTHER PUBLICATIONS

J. Organic Chem., vol. 18, pp. 127–132 (1952).

Primary Examiner—Frederick E. Waddell
Attorney, Agent, or Firm—Cushman, Darby & Cushman

[57] ABSTRACT

Compounds of the formula

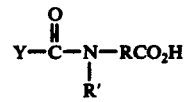

wherein Y is chlorinated alkyl of 1 to 6 carbon atoms; wherein R is $C_nH_{2n}$ or $R_2C_nH_{2n-1}$ wherein $n$ is an integer of 1 to 11 and $R_2$ is aralkyl or carboxyalky; and wherein R' is hydrogen, alkyl, haloalkyl, alkaryl or aryl; have fungicidal activity. The compounds can be used in the free acid or salt form.

13 Claims, No Drawings

HALOGENATED ACYLAMINO ACIDS AS FUNGICIDES

The present invention relates to the use of haloacylamino acids as fungicides. They possess foliar fungicidal and systemic fungicidal activity while exhibiting little phytotoxicity.

The use of fungicides in agriculture is necessitated by the fact that $3 billion is lost annually to fungus diseases in the U.S. alone. The use of fungicides results in increased yields which more than pay for the cost of the chemicals.

For every chemical discovered to have useful fungicidal activity, literally thousands have had to be screened on a variety of crops and fungi. It is vital that a fungicide not only have good fungicidal efficacy but it also must be nonphytotoxic to the plant species of concern; moreover, it is desirable that fungicides possess both protectant foliar activity and systemic activity. It is also important that a wide variety of fungi are susceptible to the chemical's activity.

The above criteria are met by the fungicides of the present invention having the formula

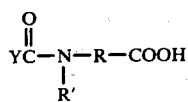

wherein Y is chlorinated alkyl of 1 to 6 carbon atoms, e.g., mono- di- and tri-chlorinated alkyl, preferably chlorinated methyl such as mono-, di-, and trichloromethyl; wherein R is $C_nH_{2n}$ or $R_2C_nH_{2n-1}$; wherein $n$ is an integer from 1 to 11, preferably 1 to 7, and R' is hydrogen, alkyl, haloalkyl, alkaryl or aryl. Preferably R' is hydrogen, alkyl of 1 to 4 carbon atoms, chloroalkyl of 1 to 4 carbon atoms, phenyl or alkylphenyl of up to 10 carbon atoms, and $R_2$ is preferably phenylalkyl of up to 10 carbon atoms or carboxylalkyl of up to 5 carbon atoms. Most preferably R' is hydrogen or methyl and R is $C_nH_{2n}$ where $n$ is 1 to 3. There can also be used salts thereof in the practice of the invention.

Typical examples of compounds which can be used in the invention are:

N-(chloroacetyl)sarcosine(alpha-chloroacetylsarcosine),
N-(trichloroacetyl)sarcosine,
N-(dichloroacetyl)sarcosine,
N-(chloroacetyl)glycine,
N-(dichloroacetyl)glycine,
N-(trichloroacetyl)glycine,
N-(chloroacetyl)valine,
N-(trichloroacetyl)valine,
N-(chloroacetyl)aspartic acid,
N-(trichloroacetyl)aspartic acid,
N-(chloroacetyl)leucine,
N-(trichloroacetyl)leucine,
N-(chloroacetyl)isoleucine,
N-(trichloroacetyl)isoleucine,
N-(chloroacetyl)norvaline,
N-(trichloroacetyl)norvaline,
N-(chloroacetyl)norleucine,
N-(trichloroacetyl)norleucine,
N-(chloroacetyl)-alpha-aminoisobutyric acid,
N-(trichloroacetyl)-alpha-aminoisobutyric acid,
N-(chloroacetyl)alanine,
N-(trichloroacetyl)alanine,
N-(chloroacetyl)phenylalanine,
N-(trichloroacetyl)phenylalanine,
N-(chloroacetyl)amino-omega-undecanoic acid,
N-(chloroacetyl)amino-omega-heptanoic acid,
N-(trichloroacetyl)amino-omega-heptanoic acid,
N-(chloroacetyl)-N-methylvaline,
N-(chloroacetyl)-N-butylglycine,
N-(trichloroacetyl)-N-ethylglycine,
N-(chloroacetyl)-N-chloromethylglycine,
N-(chloroacetyl)-N-chloroethylalanine,
N-(chloroacetyl)-N-4-chlorobutylglycine,
N-(chloroacetyl)-N-phenylbutylaminoacetic acid,
N-(chloroacetyl)-4-carboxybutylacetic acid[(N-chloroacetyl)-alpha-amino-suberic acid],
N-(chloroacetyl)-N-phenylglycine,
N-(chloroacetyl)-N-phenylalanine,
N-(trichloroacetyl)-N-phenylglycine,
N-(chloroacetyl)-N-p-tolylglycine,
N-(chloroacetyl)-N-p-t-butylphenyl glycine,
N-(2-chloropropionyl)glycine,
N-(2-chloropropionyl)sarcosine,
N-(3-chloropropionyl)glycine,
N-(3-chloropropionyl)sarcosine, N-gamma-chlorobutyrylglycine,
N-(6-chlorocaproyl)-glycine There can also be used any of the conventional salts wherein the hydrogen atom of the carboxyl acid group is replaced by a metal, an ammonium or an amine group. Thus, there can be used for example salts of an alkali metal, e.g., sodium, potassium or lithium or of an alkaline earth metal, e.g., magnesium, calcium or barium or an ammonium salt or a salt of an amine of the formula:

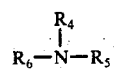

where $R_4$, $R_5$, $R_6$ may be the same or different and are suitably hydrogen, alkyl of up to 18 carbon atoms, e.g., methyl, ethyl, propyl, butyl, hexyl, decyl, dodecyl, hexadecyl, octadecyl, isopropyl, isodecyl, or aryl, e.g., phenyl or tolyl, hydroxyalkyl, e.g., hydroxyethyl and hydroxylpropyl. Suitable amines include ammonia, alkanolamines such as diethanolamine, triethanolamine, ethanolamine, dipropanolamine, isopropanolamine, dimethylamine, triethylamine, trimethylamine, methylamine, ethylamine, diethylamine, dibutylamine, octadecylamine, hexadecylamine, tributylamine, aniline, methyl phenylamine, diphenylamine, dimethylphenylamine, triphenylamine, N-methylaniline, p-methyl-aniline, dodecylamine, Specific salts include for example, the sodium salt of N-(chloroacetyl)glycine, sodium salt of N-(chloroacetyl)sarcosine, potassium salt of N-(chloroacetyl)glycine, potassium salt of N-(chloroacetyl)sarcosine, calcium salt of N-(chloroacetyl)glycine, calcium salt of N-(chloroacetyl)sarcosine, dimethylamine salt of N-(chloroacetyl)glycine, dimethylamine salt of N-(chloroacetyl)sarcosine, ammonium salt of N-(chloroacetyl)glycine, ammonium salt of N-(chloroacetyl)sarcosine, sodium salt of N-(trichloroacetyl)glycine.

The salts can be prepared in conventional fashion, e.g., the dimethylamine salt can be formed by allowing the free N-(chloroacetyl)glycine or N-(chloroacetyl)- sarcosine to stand in excess liquid dimethylamine, e.g., at 0°-5° C. or the sodium salt can be prepared by mixing a solution of N-(chloroacetyl)glycine or N-(chloroacetyl)sarcosine in methyl alcohol with a solution of sodium hydroxide in methyl alcohol.

The N-(chloroacetyl)aminocarboxylic acids per se are known in the art. They can be prepared, for example, in the manner shown in Ronwin, *J. Organic Chem.*, Vol. 18, pages 127-132. The compounds can also be prepared as shown in Example 1 hereinafter.

The fungicides and insecticides used in the practice of the invention can be used alone or they can be applied together with inert solids to form dusts, or can be suspended in a suitable liquid diluent, e.g., organic solvents or water.

There can also be added surface active agents or wetting agents and/or inert solids in the liquid formulations. In such case, the active ingredient can be from 0.01 to 95 percent or more by weight of the entire composition.

As organic solvents there can be employed hydrocarbons, e.g., benzene, toluene, xylene, kerosene, diesel fuel, fuel oil, and petroleum naphtha, ketones such as acetone, methyl ethyl ketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl Carbitol acetate and glycerine, mixtures of water and organic solvents, either as solutions or emulsions, can be employed.

The products can also be applied as aerosols, e.g., by dispersing them in air by means of a compressed gas such as dichlorodifluoromethane or trichlorofluoromethane and other Freons and Genetrons, for example.

The chlorinated compounds of the invention can also be applied with adjuvants or carriers such as talc, pyrophyllite, synthetic fine silica, attagulus clay, kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character. When a surface active agent is present, it is usually employed in an amount of 0.05 - 1% by weight.

Typical classes of surface active agents include alkyl sulfonate salts, alkylaryl sulfonate salts, alkylaryl polyether alcohols, fatty acid esters of polyhydric alcohols and the alkylene oxide addition products of such esters and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid, di(2-ethylhexyl) ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate, tertiary dodecyl polyethylene glycol thioether (Nonionic 218), long chain ethylene oxidepropylene oxide condensation products, e.g., Pluronic 61 (molecular weight 1000), polyethylene glycol ester of tall oil acids, sodium octyl phenoxyethoxyethyl sulfate, tris(polyoxyethylene) sorbitan monostearate (Tween 60), and sodium dihexyl sulfoxuccinate.

The chlorinated compounds of the invention can be employed as fungicides and insecticides using an effective amount for the intended purpose. In general, these compounds can be employed at widely varying rates. e.g., 0.1 to 100 lbs/acre, usually 0.5 to 30 lbs/acre. As fungicides, they are usually employed at a dosage of 0.1 to 20 lbs/acre. As insecticides, they are normally used in a dosage of 0.2 to 10 lbs/acre. Of course, when the compounds are used as fungicides or insecticides on growing crops, e.g., wheat, cotton, barley, soybeans, corn, oats, turnips, tomatoes, beans, peas, carrots, broccoli, beets, trees, etc., they should not be used in an amount to kill the plants. The compounds also can be applied to seeds, or fabrics, etc., as fungicides, bactericides or insecticides.

The solid and liquid formulations can be prepared by any of the conventional procedures. For example, the compounds of the present invention can be applied to soil, growing plants, e.g., trees, cotton plants, wheat and other grain plants, vegetable plants, seeds, fabrics, etc., to give fungicidal and/or insecticidal protection.

Unless otherwise indicated, all parts and percentages are by weight.

EXAMPLE 1

Synthesis of N-(Chloroacetyl)sarcosine 8.8 Grams (0.1 mole) of sarcosine was suspended in 100 ml of ethyl acetate and refluxed under anhydrous conditions with 22.6 grams (0.2 mole) of chloroacetyl chloride for 12 hours. The unreacted sarcosine was then filtered and the excess solvent and chloroacetyl chloride removed from the filtrate by vacuum distillation. The resulting oil was crystallized with the aid of a small quantity of diethyl ether. There was obtained 12.5g (76%) of N-(Chloroacetyl)sarosine whose structure was consistent with infrared analysis and element analysis for C, H, N, and Cl.

EXAMPLE 2

Synthesis of N-(Chloroacetyl)phenylalanine

10 Grams (0.06 mole) of phenylalanine was added to 125 ml of ethyl acetate and refluxed under anhydrous conditions for one hour with 7.5 ml chloroacetyl chloride. The unreacted phenylalanine was filtered and the excess chloroacetyl chloride and ethyl acetate was removed from the filtrate by vacuum distillation. A yellow oil was obtained which was crystallized with the aid of 25 ml of diethylether. There was obtained 12g (87% yield) of N-chloroacetylphenylalanine whose structure was consistent with infrared analysis and elemental analysis for C, H, N, and Cl.

EXAMPLE 3

Synthesis of N-(Chloroacetyl)-11-aminoundecanoic acid

11-Aminoundecanoic acid (10.7 grams; 0.05 mole) was added to 125 ml of ethyl acetate and refluxed with 5 ml of chloroacetyl chloride as above. After one hour no precipitate was noted and the excess chloroacetyl chloride and ethyl acetate was removed by vacuum distillation. 14 Grams (96% yield) of N-chloroacetylamino-11-undecanoic acid was obtained. This compound was confirmed by elemental analysis and infrared spectroscopy.

The fungicidal and insecticidal activities reported below were obtained employing the following general test procedures.

The alpha-(chloroacetyl)sarcosine tested was made up as a 10% solution in methanol. The solution also contained 1% dimethylformamide. The solution was sprayed on the plants at the indicated rates in the foliar fungicide tests and in the systemic fungicide tests was sprayed on the ground in which the plants were growing.

Test Procedure for Protectant Fungicidal Activity Against Late Blight of Tomatoes, *Phytopthora infestans*

Bonny Best tomato plants, Lycopersicon esculentum, approximately 5 to 6 weeks old, in five-leaf growth stage, are mounted on a compound turntable and sprayed at 30 pounds pressure with the candidate compound at concentration indicated. Samples are prepared for spraying by dissolving in a suitable solvent (e.g., methyl alcohol) and diluting to desired concentrations with deionized water containing wetting and dispersing agents.

After drying, treated plants are spray-inoculated with a mixed sporangial and zoospore suspension of *Phytopthora infestans* and immediately placed in an incubation chamber maintained at 70° F and 95% plus RH. After 40 hours in the incubation chamber, plants are removed and observed for total infection lesions of the top three leaves. Effectiveness of treatments is determined by direct comparison with inoculated controls. Maneb is used as a reference standard. All units of test include a minimum of three replicates.

Test Procedure for Protectant Fungicidal Activity Against Powdery Mildew of Cucumbers, *Erysiphe cichoracearum*

Candidate compounds are prepared for spraying by dissolving in a suitable solvent (e.g., methyl alcohol) and diluting to desired concentration with deionized water containing wetting and dispersing agents.

Straight-eight cucumber (*Cumcumis sativas*) plants in first true leaf stage, approximately 14 to 18 days old, grown under greenhouse conditions, are mounted on a compound turntable and sprayed to incipient run off at 30 psi with candidate compound at concentration indicated, using 30 ml of the spray solution per five replicates (equivalent to approximately 200 gpa).

After treated plants have dried, they are placed among diseased *Erysiphe cichoracearum* cucumber plants according to the pattern below, subjected to an initial spore shower by dusting wit- spores from diseased plants and then left undisturbed in place for approximately 10 days. By this procedure treated plants are subjected to the cited initial spore shower as well as to continuing natural infection pressure from surrounding inoculum. Observations 10 days after initial inoculation determine effectiveness of treatments. Untreated controls will generally reflect 75% to 100% leaf area diseased at this time. Effectiveness of treatment is determined by direct comparison of the average percentage leaf area infection on treated plants with the average percentage leaf area infection on untreated inoculated control. Karathane is used as a reference standard.

Test Procedure for Protectant Fungicidal Activity Against Leaf Rust of Wheat, *Puccinia rubigo-vera*

Cheyenne wheat plants, *Triticum vilgare*, approximately 7 to 8 days old and 4 to 5 inches tall are mounted on a compound turntable and sprayed at 40 pounds pressure for 60 seconds with respective candidate compounds at concentrations indicated. Candidate compounds are prepared for spraying by dissolving in a suitable solvent system, e.g., methyl alcohol and diluting to desired concentration with deionized water containing wetting and dispersing agents.

After drying, treated plants are dusted with spores of *Puccinia rubigo-vera* directly from diseased plants and then immediately placed in an incubation chamber maintained at 70° F and 95% plus RH. After the proper incubation period, plants are removed to the greenhouse for disease development.

Disease severity (infection pressure) is determined by actual count of developed pustules on inoculated but otherwise untreated controls. Control effectiveness is determined by actual count of the number of developed pustules appearing in the respective treatments compared directly to equivalent developed pustules developing an inoculated but otherwise untreated controls. Maneb is used as a reference standard. All units of test include a minimum of three replicates.

Test Procedure for Systemic Protectant Fungicidal Activity Against Powdery Mildew of Cucumbers, *Erysiphe cichoracearum*

Straight-eight cucumber plants in first true leaf stage, approximately 14–18 days old, are used as host plants. Candidate compounds dissolved in a suitable solvent system, e.g., methyl alcohol and diluted to appropriate concentrations with deionized water are applied to the soil surface of respective containers of cucumber plants which in turn are returned to the greenhouse.

Two days after treatment subject plants are placed among diseased (*Erysiphe cichoracearum*) cucumber plants, according to the pattern below, subjected to an initial spore shower by dusting with spores from diseased plants and then left undisturbed in place for approximately 10 days. By this procedure treated plants are subjected to the cited initial spore shower as well as to continuing natural infection pressure from surrounding inoculum. Observations 10 days after initial inoculation determine duration of effectiveness of treatments. Untreated controls will reflect 75% to 100% leaf area diseased at this time. Effectiveness of treatment is determined by direct comparison with untreated inoculated controls. Benlate is used as a reference standard. All units of test include a minimum of three replicates. The results of the testing are presented in Example 4 below.

EXAMPLE 4

A. Protectant Foliar Fungicidal Efficacy
% Disease
Control:

EXAMPLE 4-continued

| Disease | Plant Injury (0-10)* | Concentration |
|---|---|---|
| Late Blight | | |
| Tomato | | |
| Phytophthora infestans | 44:0 | ½ lb/acre |
| Powdery Mildew | | |
| Cucumber | | |
| Erysiphe chchoracearum | 73:0 | ½ lb/acre |
| Leaf Rust | | |
| Wheat | | |
| Pucania rubigo-vera | 20:0 | ½ lb/acre |
| B. Systemic Fungicidal Activity | | |
| Powdery Mildew | | |
| Cucumber | | |
| Erysiphe cichoracearum | 47:0 | 10 lbs/acre |
| Early Blight | | |
| Tomato | | |
| Alternaria solani | 45:0 | 10 lbs/acre |

*Plant injury was measured on a 0-10 scale with 0 denoting no injury and 10 indicating phytotoxicity.

What is claimed is:

1. A method of destroying fungi comprising applying to the fungi a fungicidally effective amount of a compound of the formula

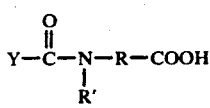

wherein Y is chlorinated alkyl of 1 to 6 carbon atoms, R is $C_nH_{2n}$ or $R_2C_nH_{2n-1}$, $n$ is an integer from 1 to 11, $R_2$ is phenylalkyl of up to 10 carbon atoms or carboxyalkyl of up to 5 carbon atoms, $R^1$ is hydrogen, alkyl, haloalkyl of 1 to 4 carbon atoms, phenyl or alkylphenyl of up to 10 carbon atoms, or a salt thereof.

2. The method according to claim 1 wherein when the compound $R^1$ is a salt it is an alkali metal, alkaline earth metal, ammonium or amine salt.

3. The method of claim 2 wherein when the salt $R^1$ is an amine salt or are ammonium salt, it has the formula

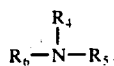

where $R_4$, $R_5$ and $R_6$ are hydrogen, alkyl of up to 18 carbon atoms, aryl, or hydroxyalkyl.

4. The method of claim 3 wherein $R_4$, $R_5$ and $R_6$ are hydrogen, alkyl of up to 18 carbon atoms, phenyl, tolyl, hydroxyethyl or hydroxypropyl.

5. The method according to claim 1 wherein Y is mono to trichloromethyl, wherein $n$ is 1 to 11, wherein $R'$ is hydrogen, alkyl of 1 to 4 carbon atoms, chloroalkyl of 1 to 4 carbon atoms, phenyl or alkylphenyl of up to 10 carbon atoms.

6. The method according to claim 5 wherein $n$ is 1 to 3, wherein $R'$ is hydrogen or methyl, and wherein $R_2$ is phenylmethyl or carboxylalkyl of up to 5 carbon atoms.

7. The method according to claim 5 wherein the nitrogen atom is one the alpha carbon to the —COOH group.

8. The method according to claim 7 wherein $n$ is 1 to 3, wherein $R'$ is hydrogen or methyl, wherein $R_2$ is phenylmethyl or carboxyalkyl of up to 5 carbon atoms.

9. The method according to claim 5 wherein the compound is in the form of the free acid.

10. The method according to claim 9 wherein the compound is alpha-chloroacetylsarcosine.

11. The method according to claim 1 wherein the compound is applied to growing plants infested with the fungi.

12. The method according to claim 1 wherein the compound is trichloroacetylsarcosine.

13. The method according to claim 1 wherein the compound is mono to trichloroacetylglycine.

* * * * *